United States Patent
Kitajima et al.

(10) Patent No.: US 11,507,127 B2
(45) Date of Patent: Nov. 22, 2022

(54) DATA GENERATION METHOD, COMPUTER-READABLE RECORDING MEDIUM, AND INFORMATION PROCESSING APPARATUS

(71) Applicant: FUJITSU LIMITED, Kawasaki (JP)

(72) Inventors: Hironobu Kitajima, Kawasaki (JP); Miho Murata, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 295 days.

(21) Appl. No.: 16/890,421

(22) Filed: Jun. 2, 2020

(65) Prior Publication Data
US 2020/0387188 A1     Dec. 10, 2020

(30) Foreign Application Priority Data
Jun. 4, 2019     (JP) .............................. JP2019-104696

(51) Int. Cl.
*G06F 1/02*       (2006.01)
*G06N 20/00*      (2019.01)
*A61B 5/316*      (2021.01)
*A61B 5/318*      (2021.01)

(52) U.S. Cl.
CPC .............. *G06F 1/022* (2013.01); *A61B 5/316* (2021.01); *A61B 5/318* (2021.01); *G06N 20/00* (2019.01)

(58) Field of Classification Search
CPC . G06F 1/02; G06F 1/022; A61B 5/316; A61B 5/318; A61B 5/327; A61B 5/349; G06N 20/00
See application file for complete search history.

(56) References Cited

U.S. PATENT DOCUMENTS

2020/0178825 A1* 6/2020 Lu .................. A61B 5/0245
2021/0093375 A1* 4/2021 Chu ................ A61B 18/1206

OTHER PUBLICATIONS

Pranav Rajpurkar et al.; "Cardiologist-Level Arrhythmia Detection with Convolutional Neural Networks"; arXiv:1707.01836v1 [cs.CV] Jul. 6, 2017; (9 pages).
J. Derek Tucker et al.; "Analysis of proteomics data: Phase amplitude separation using an extended Fisher-Rao metric"; Department of Statistics, Florida State University, Tallahassee, FL, USA; Electronics Journal of Statistics, vol. 8 (2014) 1724-1733; ISSN:1935-7524; DOI:10.1214/14-EJS900B; (10 pages).

* cited by examiner

*Primary Examiner* — Siu M Lee
(74) *Attorney, Agent, or Firm* — Staas & Halsey LLP

(57) ABSTRACT

A data generation method by a computer is disclosed. First waveform data including marking information at a first position on a waveform, and acquiring second waveform data are acquired. A transformation function is specified that transforms the first waveform data to reduce the difference between a first value of a time axis for a first characteristic point in the first waveform data and a second value of the time axis for a second characteristic point, in the second waveform data, corresponding to the first characteristic point. Third waveform data are generated, in which the marking information is applied at a second position corresponding to the first position in the first waveform data, the second position being determined by using the transformation function.

8 Claims, 17 Drawing Sheets

ELECTROCARDIOGRAM $f_2(t)$

| TIME | AMPLITUDE | ANNOTATION |
|---|---|---|
| ... | ... | ... |
| ta | 2.782 | A3 |
| tb | 2.902 | A2 |
| xx | 3.015 | |
| xx | 3.094 | |
| xx | 3.167 | |
| tc | 3.12 | A1 |
| xx | 3.072 | |
| xx | 3.010 | |
| xx | 2.948 | |
| xx | 2.628 | |
| xx | 2.268 | |
| xx | 1.897 | |
| xx | 1.525 | |
| xx | 1.144 | |
| xx | 0.759 | |
| xx | 0.387 | |
| xx | 0.023 | |
| ... | ... | ... |

ELECTROCARDIOGRAM $f'_2(t)$

| TIME | AMPLITUDE | ANNOTATION |
|---|---|---|
| ... | ... | ... |
| ta | −0.879 | |
| tb | −0.747 | |
| xx | −0.471 | |
| xx | −0.099 | |
| xx | 0.307 | |
| tc | 0.747 | |
| xx | 1.179 | |
| xx | 1.599 | |
| xx | 2.018 | |
| xx | 2.434 | |
| td | 2.782 | A'3 |
| te | 2.902 | A'2 |
| xx | 3.015 | |
| xx | 3.094 | |
| xx | 3.167 | |
| tf | 3.12 | A'1 |
| xx | 3.072 | |
| ... | ... | ... |

ELECTROCARDIOGRAM $f_1(t)$

| TIME | AMPLITUDE | ANNOTATION |
|---|---|---|
| ... | ... | ... |
| ta | −0.930 | |
| tb | −0.771 | |
| xx | −0.583 | |
| xx | −0.382 | |
| xx | 0.083 | |
| tc | 0.55 | |
| xx | 0.998 | |
| xx | 1.447 | |
| xx | 1.824 | |
| xx | 2.198 | |
| td | 2.512 | B3 |
| te | 2.819 | B2 |
| xx | 2.906 | |
| xx | 2.955 | |
| xx | 2.988 | |
| tf | 3.017 | B1 |
| xx | 2.988 | |
| ... | ... | ... |

DATA GENERATION METHOD, COMPUTER-READABLE RECORDING MEDIUM, AND INFORMATION PROCESSING APPARATUS

CROSS-REFERENCE TO RELATED APPLICATIONS

This application is based upon and claims the benefit of priority of the prior Japanese Patent Application No. 2019-104696, filed on Jun. 4, 2019, the entire contents of which are incorporated herein by reference.

FIELD

The embodiments discussed herein relate to a data generation method, a computer-readable storage medium having stored therein a data generation program, and an information processing apparatus.

BACKGROUND

Recently, a technology of an electro-cardiogram analysis using AI (Artificial Intelligence) has been developed. An electro-cardiogram (ECG) provides important information for a diagnosis of a cardiac condition. The ECG illustrates arrhythmias and an abnormal conduction of excitation. If there is a delay or an interruption of conduction in a right leg or a left leg, a unique ECG pattern is illustrated. It is also known that an ST portion and a T wave in the ECG are altered from a normal waveform in a patient with angina pectoris or a myocardial infarction.

The ECG analysis using AI is known to use annotated data to accurately classify the arrhythmias by a deep learning.

[Non-Patent Document 1]
Rajpurkar P et al., "Cardiologist-Level Arrhythmia Detection with Convolutional Neural Networks", 6 Jul. 2017.

SUMMARY

According to one aspect of the embodiments, a data generation method executed by a computer, the data generation method including acquiring first waveform data and second waveform data, each of the first waveform data and the second waveform data including marking information at a first position on a waveform; specifying a transformation function that transforms the first waveform data to reduce the difference between a first value of a time axis for a first characteristic point in the first waveform data and a second value of the time axis for a second characteristic point, in the second waveform data, corresponding to the first characteristic point; and generating third waveform data, in which the marking information is applied at a second position corresponding to the first position in the first waveform data, the second position being determined by using the transformation function.

The object and advantages of the invention will be realized and attained by means of the elements and combinations particularly pointed out in the claims.

It is to be understood that both the foregoing general description and the following detailed description are exemplary and explanatory and are not restrictive of the invention, as claimed.

BRIEF DESCRIPTION OF DRAWINGS

Other objects, features and advantages of the present invention will become more apparent from the following detailed description when read in conjunction with the accompanying drawings, in which.

DESCRIPTION OF EMBODIMENTS

Prior to describing the embodiments in detail, brief explanation of technical problems in the existing technology found by the inventor will be provided. In order to improve the accuracy of an electro-cardiogram (ECG) analysis by AI, a sufficient number of non-normal ECGs such as arrhythmias are obtained; however, there is a problem that the ECG is not given with an annotation, which is a major factor in the analysis, or that the ECG with insufficient annotation is difficult to use as learning data.

There is a problem with an inability to accurately perform ECG-based learning because of insufficient available learning data on a certain type of a disease to be accurately classified.

Accordingly, in an embodiment described below, a technical scheme will be presented to optimize waveform data, to which marking information is applied.

The embodiment will be described with reference to the drawings. Data extension techniques are often used as a means for artificially increasing the amount of training data for a machine learning in order to obtain sufficient data for the ECG analysis by AI. A data augmentation is specifically a technique that artificially increases the amount of the training data by transforming the data by applying, for example, a parallel shift, a rotation, a scale transformation, a mirror projection, or the like with respect to a small number of the training data.

The data augmentation for ECG by known transformations are somewhat effective, but have limitations. For instance, The accuracy of an inference is not improved beyond a certain level, even if training data are largely increased by a homogeneous transformation and learned.

Simple geometric transformations may create an unrealistic ECG.

The embodiment provides a technique for generating natural waveform data as a human ECG, artificially increasing an amount of the training data (referred to as "extending of training data" or "data augmentation"), and providing markings imparted by those with expertise to generated waveform data to improve learning efficiency. A marking corresponds to a segment of an element waveform, a mark at a peak of the element waveform, or the like. The marking is applied to an ECG waveform by a physician with expertise in reading actual ECGs.

Figure 1:
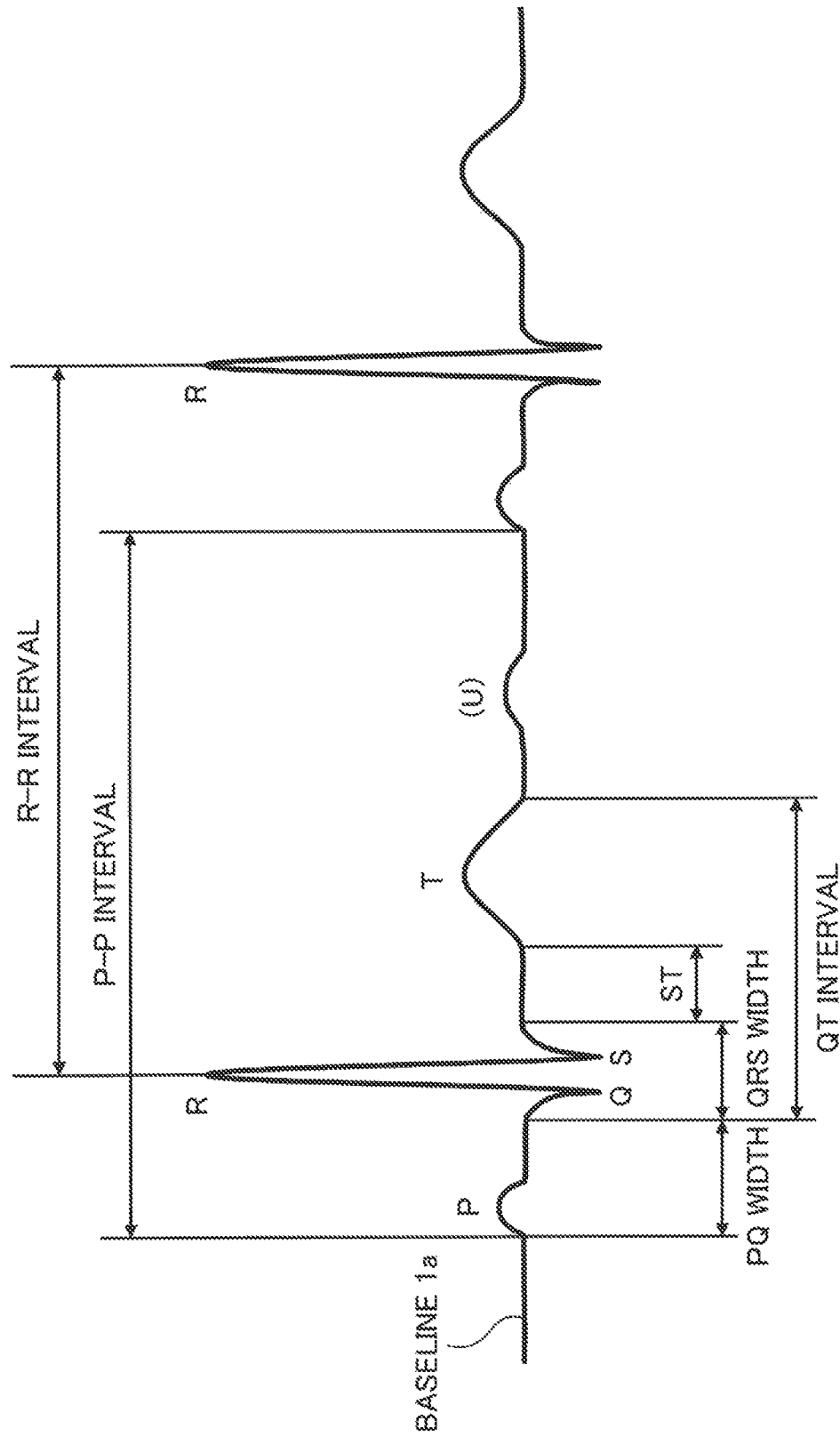
FIG. 1 is a diagram illustrating an ECG waveform.

FIG. 1 is a diagram illustrating an ECG waveform. As depicted in FIG. 1, the ECG waveform represents a series of waveforms, called a P wave, a QRS complex, a T wave, and a U wave, in which an excitation originating from a sinus node spreads throughout a heart and a variation from a baseline 1a is seen on an ECG with each sinus contraction. The waveforms are regarded as major element waveforms of the ECG.

Because of the nature of an ECG, the major element waveforms are preferably maintained in a created ECG. Also, changes in a PQ interval and a QT interval on the ECG represent a collective propagation of action potentials in cells. The time span of each element waveform may be used to identify an abnormal propagation time, which is likely to appear in a part of an ECG related to the heart disease. In order to increase the amount of the training data in the vicinity of the abnormal state, the start time and the end time of each of the element waveforms in an actual ECG waveform may be flexibly changed within a certain degree to allow an expansion or a contraction in a time axis.

However, it is not possible to generate a waveform, in which element waveforms of the P wave, the QRS wave, and the T wave are similar to each other but PQ intervals or QT intervals indicate different terms, by a simple geometric transformation.

In response to the problems described above, the inventors have found a method for retaining main element waveforms of the ECG, and transforming from the actual ECG waveform to the natural ECG waveform as a human ECG.

First, the inventors used an Elastic Shape Analysis (ESA) technology. By using the ESA technology, two waveforms may be shifted on a time axis to approximate their shapes to each other as smoothly as possible (a continuous function is obtained).

in a case of using acquired transformation, as many waveforms as desired may be generated to interpolate between two actual ECG waveforms, because the annotation of the training data is a point on a waveform, the same annotation is applied to a created waveform by shifting a position of the point using the same transformation. The annotation is regarded as information, which is marked with respect to a particular point in the waveform data.

Moreover, the embodiment creates the waveform data, which approximates the natural human ECG. In order to achieve this goal, (a) two types of the ECG data are selected (pre-process).

As an example, the two types to be selected may be one ECG representing a normal state of a heart and another ECG representing an abnormal state of the heart. By selecting at least one ECG in the abnormal state, it is possible to increase an amount of the training data in variations of the abnormal state, and it is also possible to generate ECG data near a boundary between the normal state and the abnormal state. The selection may be random, and depending on a desired type, both may represent the normal state or both may represent the abnormal state.

First, as preparations, (a-1) A range is determined to be cut out from each of selected ECGs. As one example, an integral multiple of one beat, two beats, or the like, is preferred. Respective peaks of two R waves may be detected and one beat may be determined by one R-R interval or a range shifted by half the R-R interval. An R wave may be identified by reference to markings or by detection of the R wave using an existing open tool, which automatically detects the R waves. The P-P interval may also be used for a cut-out range.

(a-2) A transverse width of a partial waveform cut out from each of the selected ECGs is normalized to match a heart rate, and two partial waveforms corresponding to the selected ECGs are referred to as an ECG $f_1(t)$ and an ECG $f_2(t)$, or simply referred to as $f_1(t)$ and $f_2(t)$.

Next, a waveform (that is, electro-cardiogram data) is generated that interpolates between the selected two ECG waveforms, that is, between $f_1(t)$ and $f_2(t)$.

(b) with respect to $f_1(t)$ and $f_2(t)$, an extension or a contraction of the time axis (change in a phase direction) is performed to match positions of peaks and valleys of the partial waveforms, or an alignment process is performed to reduce the difference between values of the time axis.

(c) one or more waveforms are generated to interpolate between $f_1(t)$ and $f_2(t)$ by changing a width in the phase direction and a height in an amplitude direction.

Furthermore, in the embodiment, annotations are provided for each of the generated waveforms.

(d) by using a transformation for each change in the phase direction and the amplitude direction, annotations are imparted on each of the generated waveforms.

The above-described processes (a) to (d) are implemented by a data generating apparatus having a hardware configuration as described below.

Figure 2:
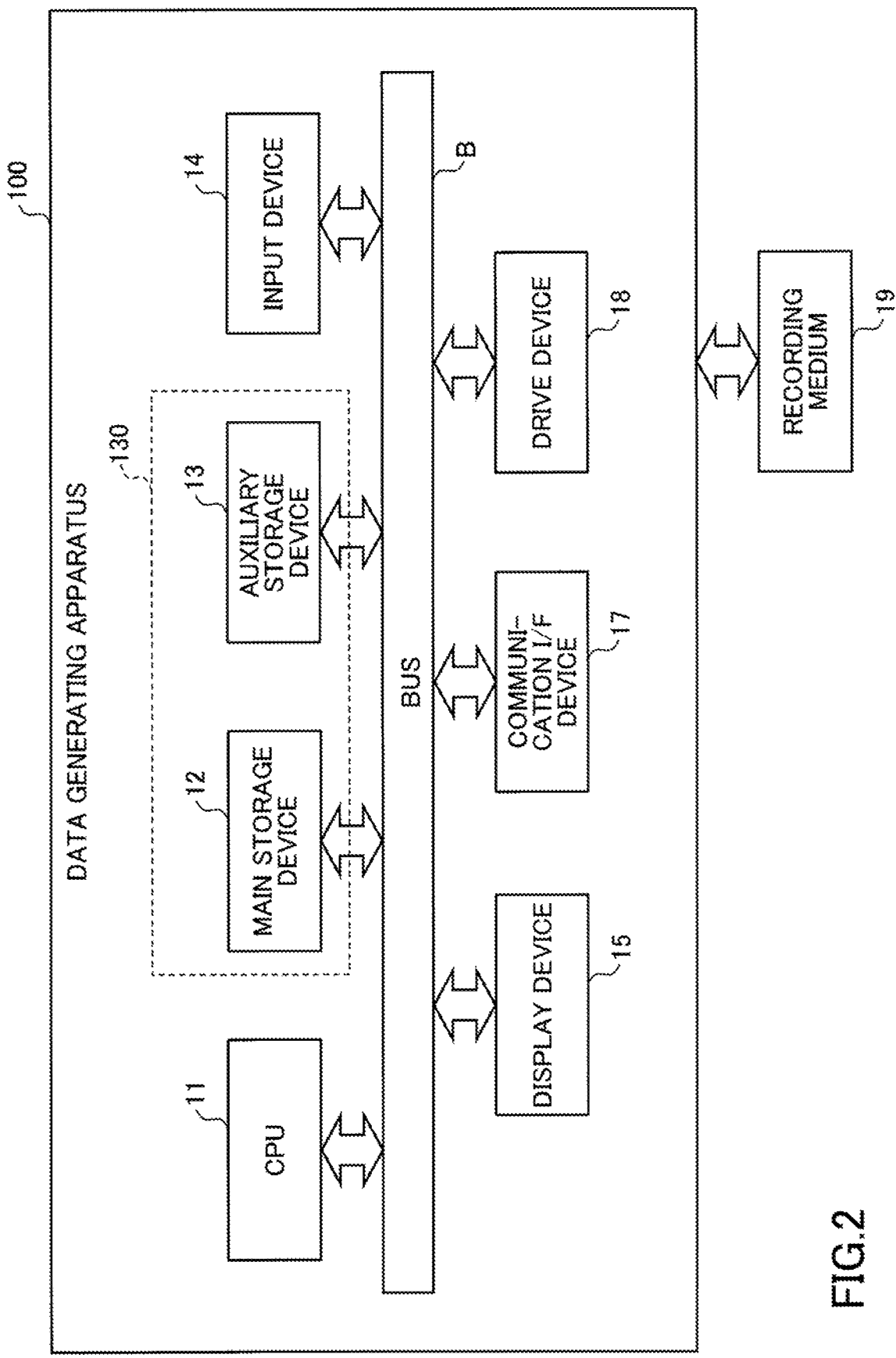
FIG. 2 is a diagram illustrating an example hardware configuration of a data generating apparatus according to the embodiment.

FIG. 2 is a diagram illustrating an example of a hardware configuration of the data generating apparatus according to the embodiment. In FIG. 2, the data generating apparatus 100 is an information processing apparatus including a Central Processing Unit (CPU) 11, a main storage device 12, an auxiliary storage device 13, an input device 14, a display device 15, a communication I/F device 17, and a drive device 18, which are connected to a bus B. The main storage device 12, the auxiliary storage device 13, and an external storage device, which is accessed by the data generating apparatus 100, are referred to as a storage part 130.

The CPU 11 corresponds to a processor controlling the data generating apparatus 100, executes a program stored in the storage part 130, and realizes various processing according to the embodiment as described below. The input device 14 is operated by a user and inputs data in response to operation, and the display device 15 displays various screens as a user interface. The communication I/F device 17 controls communication with an external device.

A program for implementing processes according to the embodiment, stored in a recording medium 19 (for instance, a Compact Disc Read-Only Memory (CD-ROM)), is installed in the storage part 130 via the drive device 18 and is executable by the CPU 11.

The recording medium 19 of the program according to the embodiment is not limited to the CD-ROM, but may be one or more non-transitory and tangible medium having a structure readable by a computer. As the computer readable storage medium, in addition to the CD-ROM, a portable storage medium such as a Digital Versatile Disk (DVD) disk, a USB memory, or a semiconductor memory such as a flash memory may be used.

Figure 3:
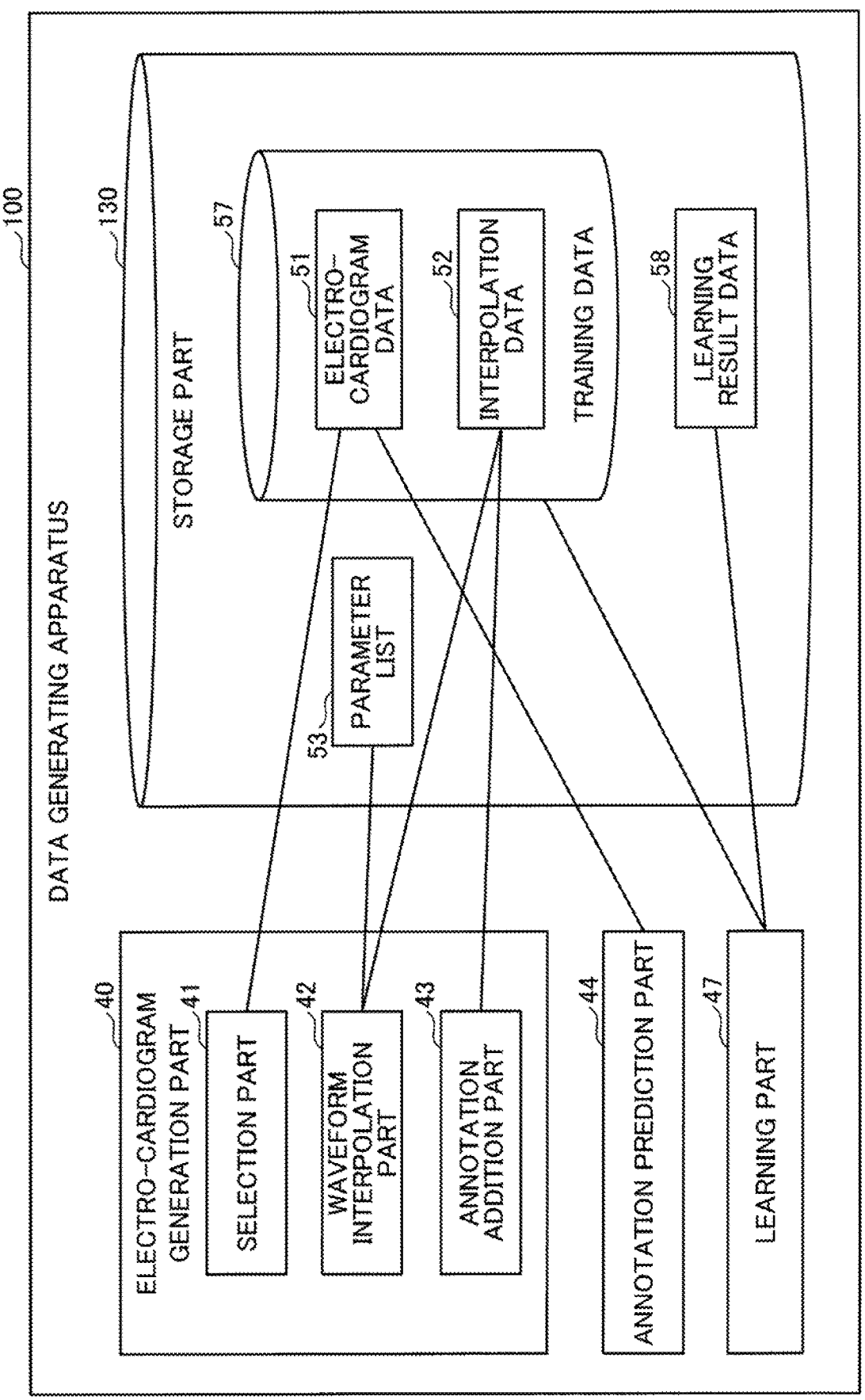
FIG. 3 is a diagram illustrating an example functional configuration of the data generating apparatus.

FIG. 3 is a diagram illustrating an example of a functional configuration of the data generating apparatus. In FIG. 3, the data generating apparatus 100 mainly includes an electro-cardiogram generation part 40, an annotation prediction part 44, and a learning part 47. The electro-cardiogram generation part 40, the annotation prediction part 44, and the learning part 47 are realized by processes, in which corresponding programs installed in the data generating apparatus 100 are executed by the CPU 11 of the data generating apparatus 100. The storage part 130 stores a parameter list 53, training data 57, learning result data 58, and the like.

The electro-cardiogram generation part 40 generates a natural waveform as a human ECG based on the actual electro-cardiogram data 51, and performs an ECG generation process to interpolate the training data 57. The electro-cardiogram generation part 40 further includes a selection part 41, a waveform interpolation part 42, and an annotation addition part 43.

The selection part 41 performs a selection process. In the selection process, two pieces of data are selected from among the electro-cardiogram data 51 in the training data 57. A waveform is cut out based on a range determined by a predetermined interval and by a heart rate from each of the selected two pieces of data. Then, each of cut-out partial waveforms is sent to the waveform interpolation part 42. The cut-out partial waveforms of the ECGs are an ECG $f_1(t)$ and an ECG $f_2(t)$ or simply referred to as $f_1(t)$ and $f_2(t)$.

The waveform interpolation part 42 converts, based on the parameter list 53, one or more of phases and amplitudes of one of $f_1(t)$ and $f_2(t)$ waveforms into a waveform, which is changed to approximate another waveform, and performs a waveform interpolation process to generate an interpolated ECG (interpolation data 52). The waveform interpolation part 42 also causes the annotation addition part 43 to apply an annotation each time the interpolation data 52 are generated. The interpolation data 52 associated with the annotation are added to the training data 57.

The annotation addition part 43 performs the process for adding annotations, which are present in the source waveform, to a corresponding position on the interpolated waveform represented by the interpolation data 52, by a similar transformation used by the waveform interpolation part 42 each time the interpolation data 52 are generated. The annotation addition process may be performed only on a specified interpolation data 52.

The annotation prediction part 44 predicts a position (coordinates on a waveform) where an annotation is to be applied, with respect to each piece of the electro-cardiogram data 51 that has insufficient annotations, and supplements information of the annotation.

The learning part 47 learns to distinguish normal conditions from abnormal conditions of the heart based on various ECGs using the training data 57, of which the amount is increased by the interpolation data 52 obtained in accordance with the embodiment. By adding the interpolation data 52 to the training data 57, it is possible for the learning part 47 to improve the accuracy in determining the presence of the heart disease, and to further realize a detailed classification of the heart disease.

The training data 57 includes the interpolation data 52 added according to the embodiment in addition to the electro-cardiogram data 51 actually obtained from a person by using an electrocardiograph. The plurality of pieces of the electro-cardiogram data 51 may include data to which an annotation has been applied and data to which no annotation has been applied. Also, in the electro-cardiogram data 51 where annotations have been applied, various element waveforms may be annotated by the information of the annotations.

The parameter list 53 illustrates a set of values of a parameter "k" for transforming a waveform between phases of the two pieces of the electro-cardiogram data 51 and of a parameter "l" for changing the waveform between amplitudes of the two pieces of the electro-cardiogram data 51. The parameters "k" and "l" indicate values of 0 or more and 1 or less, respectively.

The learning result data 58 includes data such as weight information obtained by the learning part 47 using the training data 57.

Figure 4:
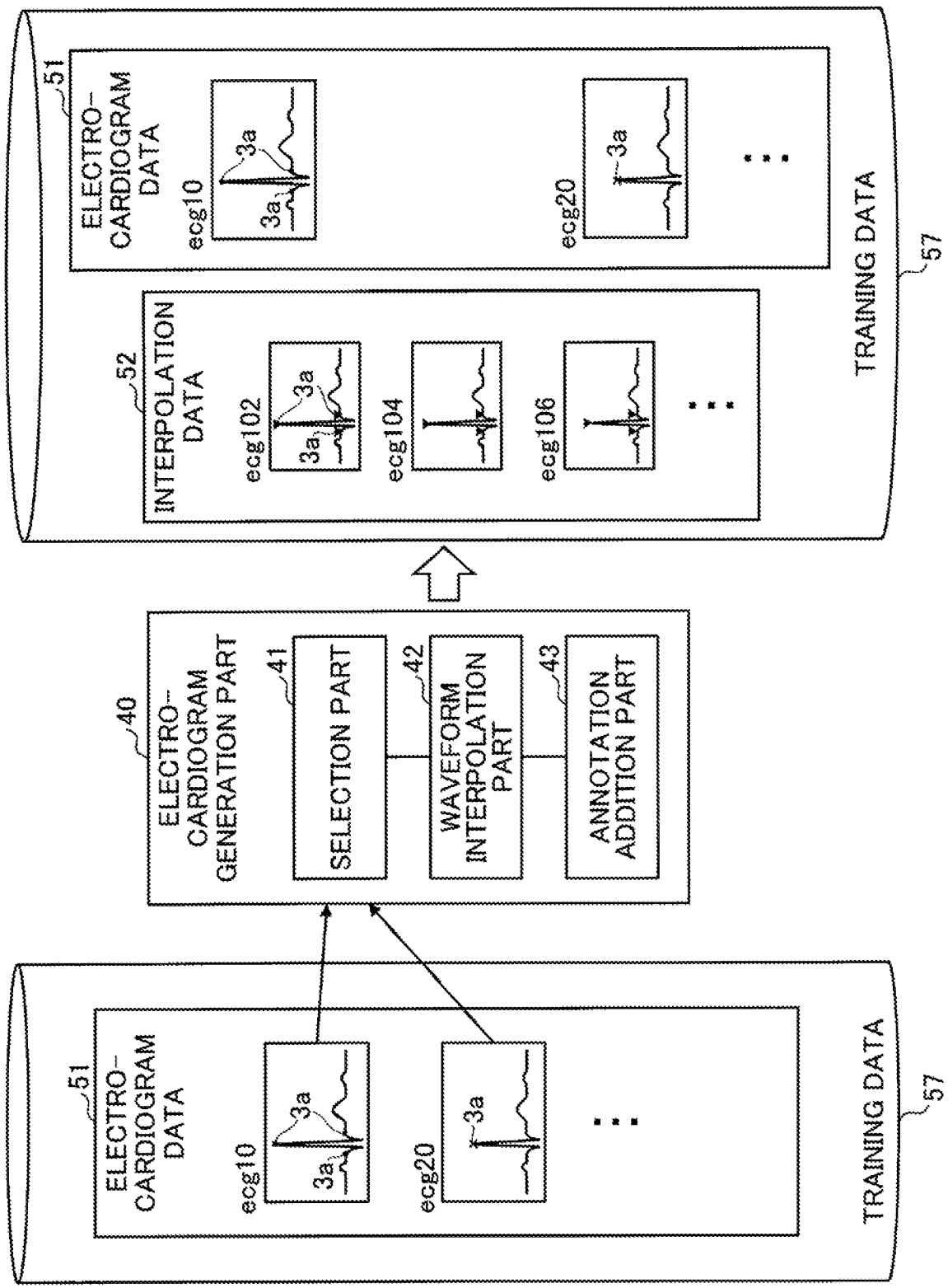
FIG. 4 is a diagram for briefly explaining an electro-cardiogram generating process according to the embodiment.

FIG. 4 is a diagram for briefly explaining the ECG generation process according to the embodiment. As illustrated in FIG. 4, two pieces of ECG data ecg10 and ECG data ecg20 are selected by the electro-cardiogram generation part 40 from the plurality of pieces of the electro-cardiogram data 51. As an example, the normal state and the abnormal state of the heart are selected.

In FIG. 4, a case example, in which the ECG data ecg10 includes three annotations 3a (FIG. 5), while the ECG data ecg20 includes only one annotation 3a, is illustrated. In the ECG data ecg10, the annotations 3a are indicated by a mark "•", and in the ECG data ecg20, the annotation 3a is indicated by a mark "x".

The electro-cardiogram generation part 40 generates a plurality of pieces of waveform data for each of combinations of parameters (k, l) in the phase direction and the amplitude direction of the ECG data ecg10 to approach the ECG data ecg20, and outputs waveform data as interpolation data ecg102, ecg104, ecg106, or the like to be added to the training data 57.

In the embodiment, the annotation 3a is also applied to the interpolation data 52 output from the electro-cardiogram generation part 40. In this example, annotations applied by the electro-cardiogram generation part 40 are indicated by a mark "▼" to easily identify points of the applied annotations. The annotations for the interpolation data 52 may be based on the electro-cardiogram data ecg10 having more annotations 3a.

Figure 5:
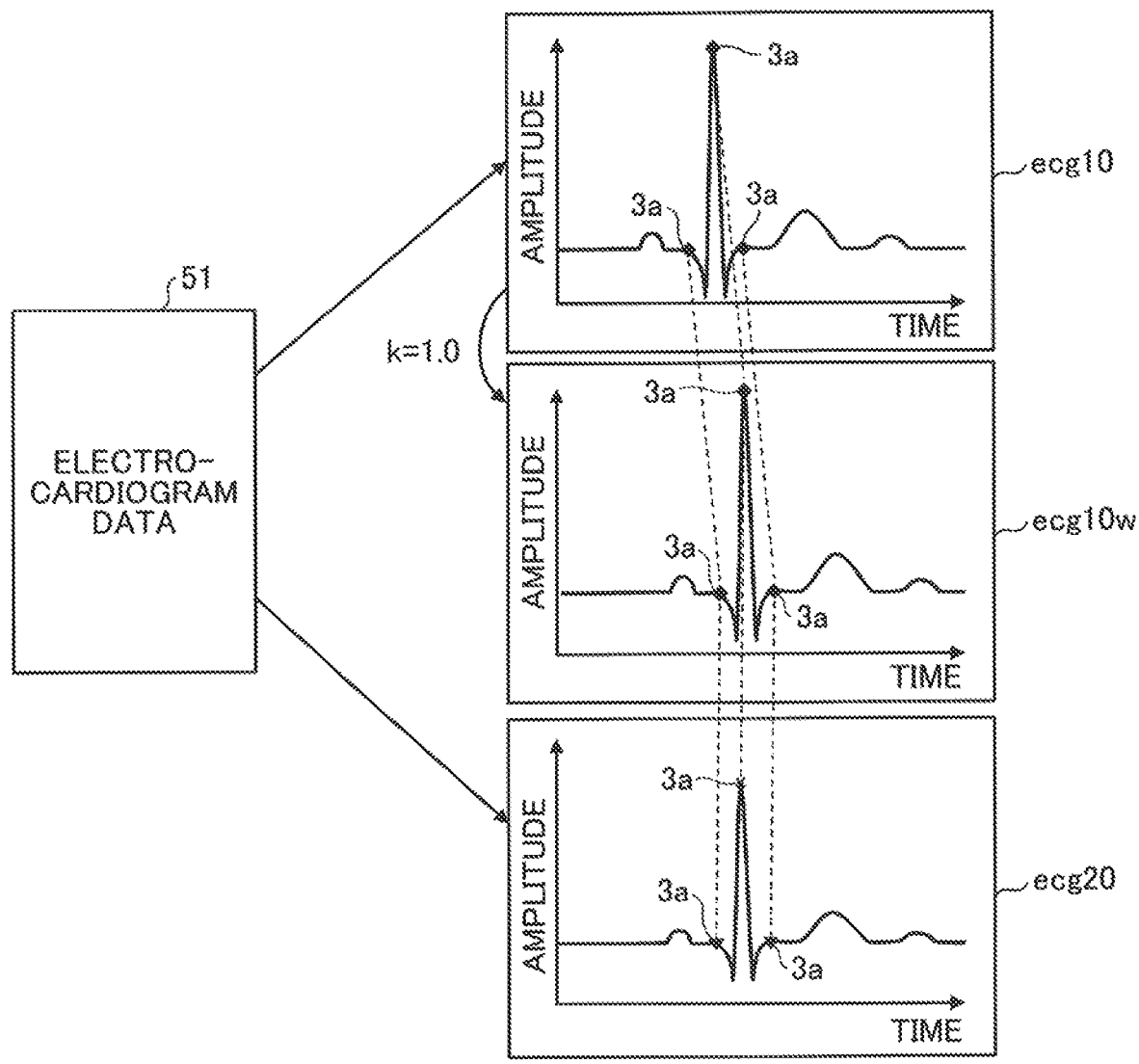
FIG. 5 is a diagram for briefly explaining an annotation predicting process according to the embodiment.

FIG. 5 is a diagram for briefly explaining an annotation predicting process according to the embodiment. In FIG. 5, an example is illustrated, in which two annotations 3a are added to the ECG data ecg20 based on the ECG data ecg10 having more annotations 3a among the two ECG data ecg10 and ecg20 selected from the electro-cardiogram data 51. The added annotations 3a are indicated by "▼".

The annotation prediction part 44 sets the parameter "k" in the phase direction to 1.0, aligns positions of the annotation 3a of the ECG data ecg10 to correspond to a phase of the ECG data ecg20, and obtains the ECG data ecg10w. The annotation prediction part 44 calculates positions on the ECG data ecg10w corresponding to the positions of the annotation 3a on the ECG data ecg10 by the same transformation used for the alignment, and applies the annotations 3a at the calculated positions.

The positions of the three annotations 3a are specified by the time and the amplitude. The annotation prediction part 44 provides three annotations 3a for the ECG data ecg10w at times corresponding to the positions of the three annotations 3a of the ECG data ecg10w. Here, the annotation prediction part 44 may omit the application of one or more annotations 3a already present in the ECG data ecg20 to respective one or more positions among the three annotations 3a of the ECG data ecg10w.

In the example, with respect to the two ECG waveforms, a transform is performed to change one of or both the phase direction and the amplitude direction to generate, and a plurality of waveforms are generated in a range defined by a difference between temporal widths and a difference between amplitudes of the element waveforms to interpolate between the two ECG waveforms.

Figure 6:
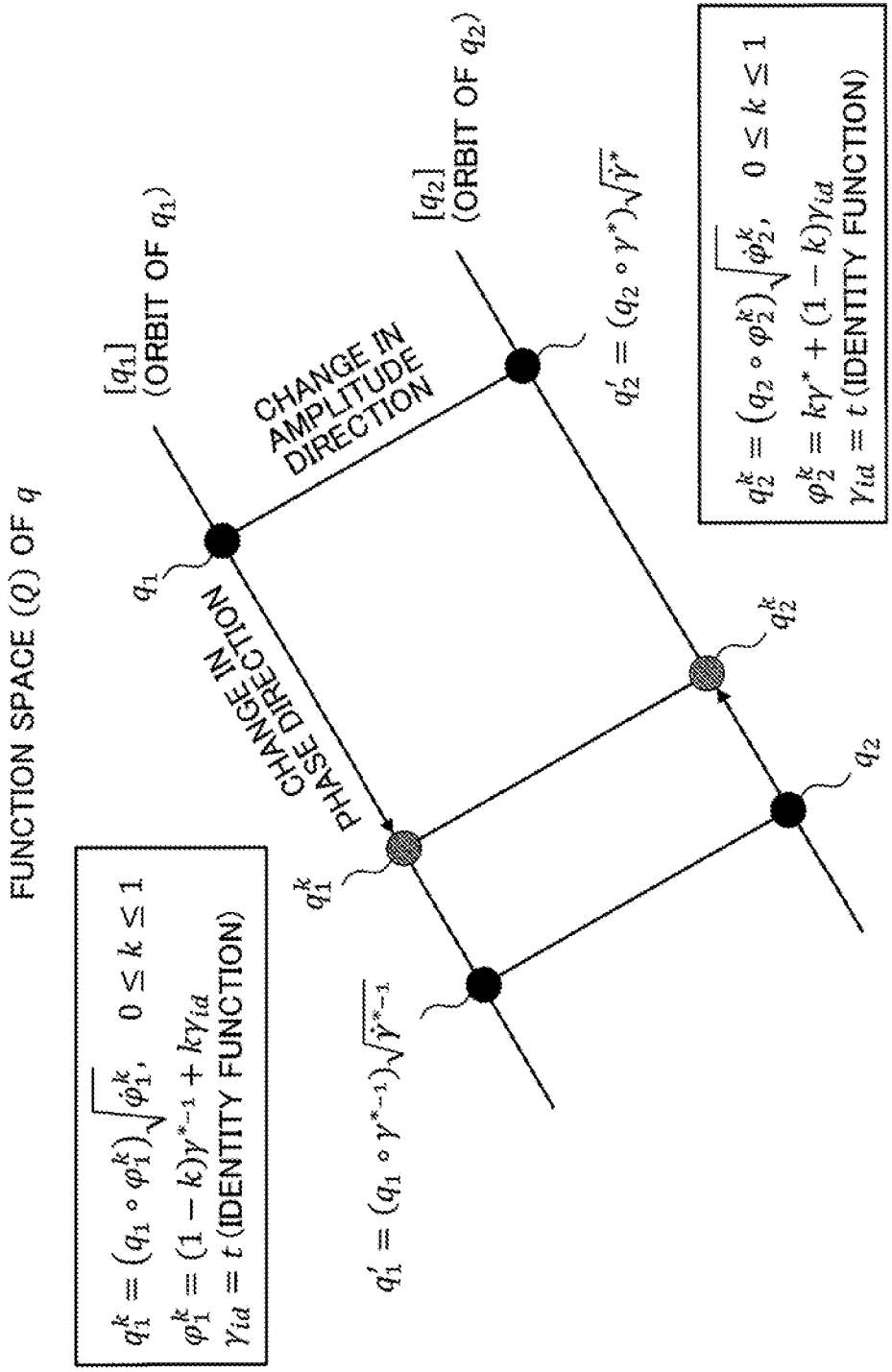
FIG. 6 is a diagram for explaining an example of a function space considered in the embodiment.

FIG. 6 is a diagram for explaining an example of a function space considered in the embodiment. With reference to FIG. 6, processes performed by the waveform interpolation part 42, the annotation addition part 43, and the annotation prediction part 44 will be described.

<Waveform Interpolation Method>

A method for generating interpolated ECG data (interpolation data 52) based on an Elastic Shape Analysis (ESA) framework is described below. The ESA considers a function space F of a curve representing data and a space Q of a function called Square-Root Slope Function (SRSF), to which the function space F is mapped.

A function of the time-series ECG data is represented by

[Formula 1]

$$f(t) \in \mathcal{F}.$$

In a case in which a function for mapping this function to the SRSF is represented by

[Formula 2]

$$q(t) \in Q,$$

these functions f(t) and q(t) have a relationship represented by the following expression (1):

[Formula 3]

$$q(t) = \text{sign}(\dot{f}(t))\sqrt{|\dot{f}(t)|},$$

sign(•) denotes a signum function,
$\dot{f}(t)$ denotes a time derivative of f(t)

$$f(t) = f(0) + \int_0^t q(s)|q(s)|ds \qquad (1).$$

The functions f(t) and q(t) are able to be mutually converted.

Here, it is considered that two ECGs $f_1(t)$ and $f_2(t)$ and functions $q_1(t)$ and $q_2(t)$ mapped above to the SRSF (FIG. 6).

Figure 9:
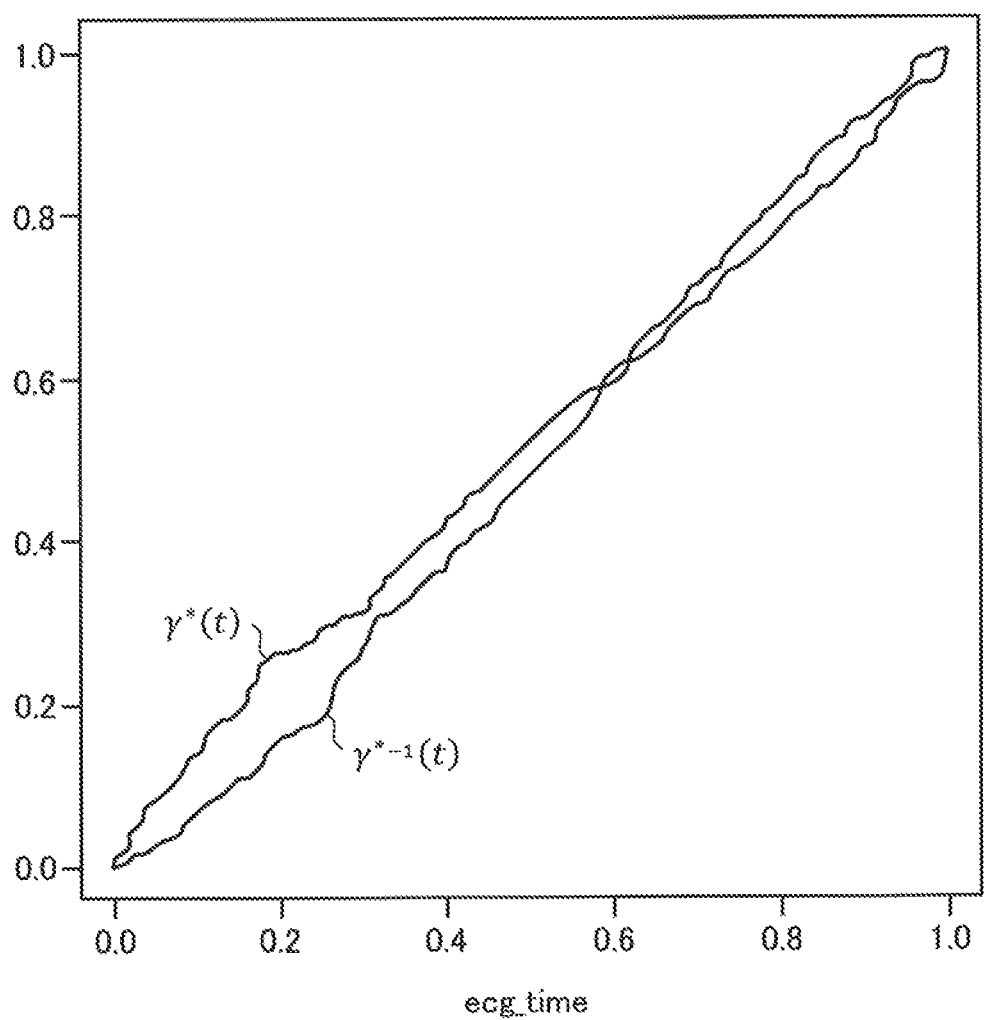
FIG. 9 is a diagram illustrating an example of a warping function in FIG. 7 and FIG. 8.

Moreover, under the framework of the ESA, an alignment process is performed, in which $f_2(t)$ is used as a start point with respect to $f_1(t)$ and positions of peaks and valleys of the waveforms are matched as much as possible, and a warping function $\gamma^*(t)$ and an inverse function $\gamma^{*-1}(t)$ are obtained (FIG. 9). The warping function $\gamma(t)$ is a continuous function that represents an extension and a contraction (change in the phase direction) of the time axis. An optimized warping function in the above alignment is represented by $\gamma^*(t)$, which is obtained as a solution to the following optimization problem in Q.

[Formula 4]

$$\gamma^* = \arg\inf_{\gamma \in \Gamma} \|q_1 - (q_2, \gamma)\| \; (\Gamma: \text{set of warping functions}, \| \; \| : L^2 \text{norm}) \quad (1.1)$$

$$(q_2, \gamma) =$$

$$(q_2 \circ \gamma)\sqrt{\dot{\gamma}} = q_2(\gamma(t))\sqrt{\dot{\gamma}(t)} \; (\circ \text{ denotes function composition}).$$

In this case, $f_1(t)$ and $f_2(\gamma^*(t))$ have a relationship, in which shapes of curves are aligned, and a point (functions) $q_1$ and a corresponding point $q_2'$ on Q face each other on two parallel straight lines $[q_1]$ and $[q_2]$ representing respective orbit of $q_1$ and $q_2$ with the warping function $\gamma(t)$.

Figure 7:
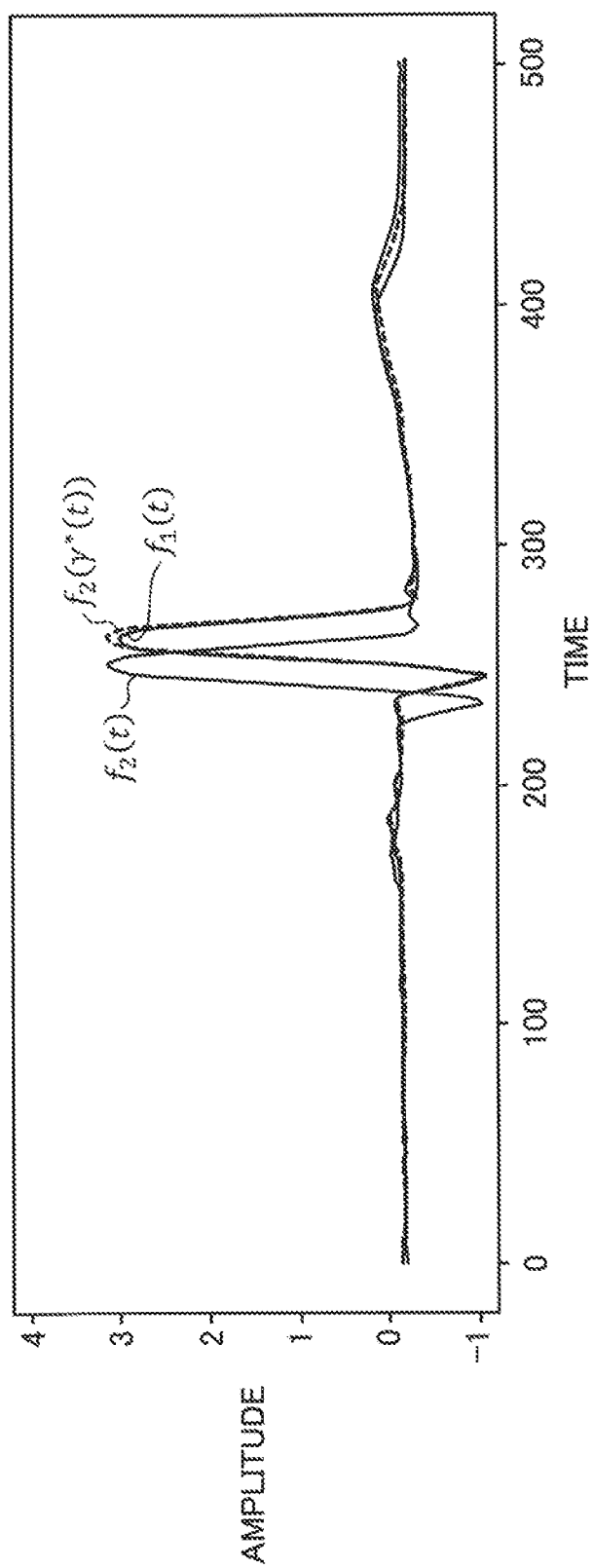
FIG. 7 is a diagram illustrating an example of an alignment in the embodiment.
Figure 8:
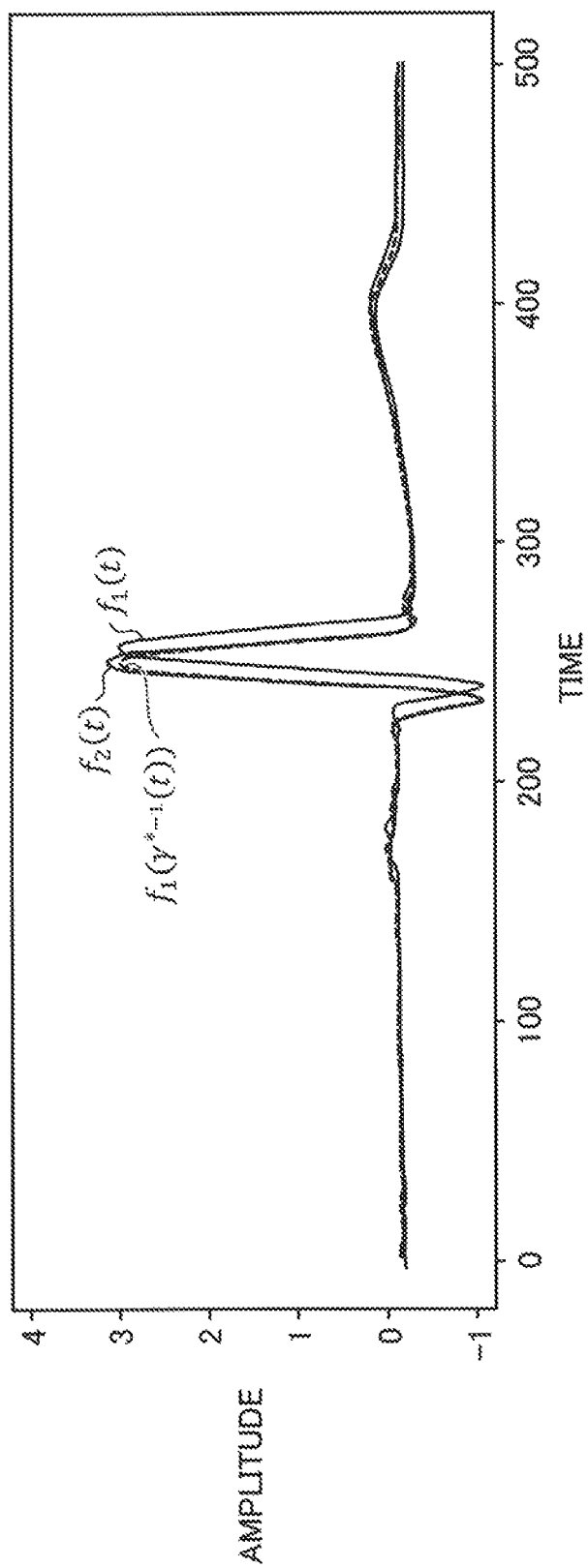
FIG. 8 a diagram illustrating another example of the alignment in the embodiment.

Alternatively, it is possible to perform the alignment process starting from $f_1(t)$ with reference to $f_2(t)$. In this case, $f_1(\gamma^{*-1}(t))$ and $f_2(t)$ are aligned, and a point $q_1'$ and a corresponding point $q_2$ on Q still face each other. FIG. 7 illustrates an example in which $f_2(\gamma^*(t))$ is calculated with reference to $f_1(t)$. FIG. 8 illustrates an example, in which $f_1(\gamma^{*-1}(t))$ is calculated based on $f_2(t)$. Another example of the warping functions $\gamma^*(t)$ and $\gamma^{*-1}(t)$ is illustrated in FIG. 9.

A function (q, γ) is acquired by mapping the function f(γ(t)), in which the time axis of the function f(t) is extended by the warping function γ(t), to Q, and is expressed as follows:

[Formula 5]

$$(q, \gamma) = (q \circ \gamma)\sqrt{\dot{\gamma}} = q(\gamma(t))\sqrt{\dot{\gamma}(t)}$$

(○ denotes function composition).

By using the above formula 5, the points (functions) $q_1'$ and $q_2'$ respectively on the lines $[q_1]$ and $[q_2]$ in FIG. 6 are expressed as follows:

[Formula 6]

$$q'_1 = (q_1 \circ \gamma^{*-1})\sqrt{\dot{\gamma}^{*-1}}$$

$$q'_2 = (q_2 \circ \gamma^*)\sqrt{\dot{\gamma}^*}. \qquad (2)$$

Considering the generation of interpolated ECGs representing a smooth change between the two actual electrocardiograms, we define the following function $\varphi_2^k$.

[Formula 7]

$$\varphi_2^k = k\gamma^* + (1-k)\gamma_{id}, \gamma_{id} = I, 0 \le k \le 1$$

$$q_2^k = (q_2 \circ \varphi_2^k)\sqrt{\dot{\varphi}_2^k}. \qquad (3)$$

In the above description, $\varphi_2^k$ is a function, in which an identity function $\gamma^{id}$ and the function $\gamma^*$ transferring $q_2$ to $q_2'$ are proportionally distributed by the parameter k. Also, $\varphi_2^0$ corresponds to $\gamma^{id}$ ($\varphi_2^0 = \gamma^{id}$) and $\varphi_2^1$ corresponds to $\gamma^*$ ($\varphi_2^1 = \gamma^*$). The function φ meets requirements of the warping function in the ESA. Moreover, $q_2^k$, which is a point (function) where $q_2$ is mapped by $\varphi_k$, is on the line $[q_2]$ having ends of $q_2$ and $q_2'$ and corresponds to the interpolated electro-cardiogram $f_2$ ($\varphi_2^k(t)$).

Next, $q_1$ is shifted to align with respect to $q_2^k$ and is denoted by $q_1^k$. $q_1^k$ opposite to $q_2^k$ is calculated by the following expression based on a position relationship on Q.

$$q_1^k = (q_1 \circ \gamma^{*-1} \circ \varphi_2^k) \sqrt{\frac{d}{dt}(\gamma^{*-1} \circ \varphi_1^k)}$$ [Formula 8]

$$\gamma^{*-1} \circ \varphi_w^k = \gamma^{*-1} \circ (k\gamma^* + (1-k)\gamma_{id}) = k\gamma_{id} + (1-k)\gamma^{*-1}$$ [Formula 9]

Thus, $q_1^k$ may be expressed as follows:

[Formula 10]

$$q_1^k = (q_1 \circ \varphi_1^k) \sqrt{\varphi_1^k}$$

$$\varphi_1^k = k\gamma_{id} + (1-k)\gamma^{*-1} \quad (4)$$

Comparing an expression (3) with an expression (4), as seen from an expression $q_1^k$ and an expression $q_2^k$, $\gamma^{*-1}$ and $\gamma^{*-1}$ are mutually replaced, and an inverse ratio of a proportional distribution is expressed. Accordingly, the interpolated ECG generated from a side of $q_1$ is represented by $f_1(\varphi_1^k(t))$.

Figure 10:
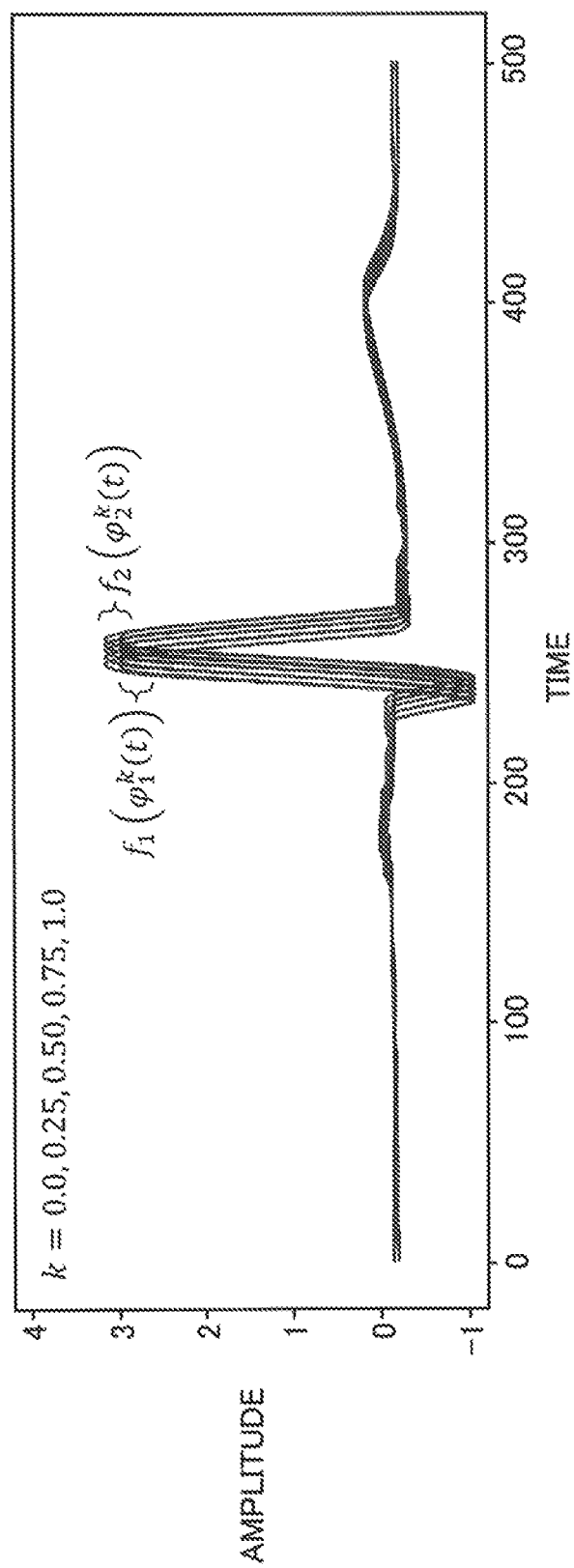
FIG. 10 is a diagram illustrating an example of an alignment in a phase direction and interpolation.

In the above, ECG waveforms are interpolated in the phase direction by using warping functions such as $\varphi_1^k$ and $\varphi_2^k$. FIG. 10 illustrates how the alignment and the interpolation in the phase direction is performed by representing behaviors of $f_1(\varphi_1^k(t))$ and $f_2(\varphi_2^k(t))$ when k is changed to 0.0, 0.25, 0.50, and 1.0.

In the following, the interpolation of the waveform in the amplitude direction will be described.

The functions $f_1(\varphi_1^k(t))$ and $f_2(\varphi_2^k(t))$ which have been already aligned in the phase direction, may be defined by a function of a convex combination as follows:

[Formula 11]

$$f^{k,l}(t) = lf_1(\varphi_1^k(t)) + (1-l)f_2(\varphi_2^k(t)), 0 \le k \le 1, 0 \le l \le 1 \quad (5)$$

By this expression (5), an interpolation in an amplitude direction is conducted. The functions $f_1(\varphi_1^k(t))$ and $f_2(\varphi_2^k(t))$ have been already aligned and characteristic element waveforms such as P, QRS, and T waves (FIG. 1) occur in approximately the same region on a horizontal axis (FIG. 10). That is, it is possible to generate one or more natural ECGs by using a simple convex combination such as $f^{k,l}(t)$.

As described above, it is possible to automatically generate large quantities of natural ECGs $f^{k,l}(t)$ by selecting appropriate actual ECGs $f_1(t)$ and $f_2(t)$ and parameters "k" and "l", and interpolating in each of the phase direction and the amplitude direction.

In this example, the interpolation of waveforms is restricted in a region with $q_1$, $q_2$, $q_1'$, and $q_2'$ as vertices illustrated in FIG. 6. By this restriction, it is possible to eliminate unnatural conditions that do not exist as any state of the human heart. Unnatural conditions correspond to element waveforms that exhibit an unusually large amplitude or an unusually large duration. In a case of interpolating the training data 57 with data containing unnatural conditions, the learning will not be properly conducted.

<Annotation Method>

An annotation applied by a person to an ECG is given in order to indicate one of characteristic points on the waveform and also to identify a certain interval formed by the characteristic points in the waveform. Accordingly, the annotation is applied as a point on the waveform, and if a function to convert the waveform is known, it is possible to determine the position (point) of the annotation at the same time.

For instance, in a case in which an annotation is located at a point of a time $t_a$ on the ECG $f_2(t)$, an annotation position is projected by the expression (5) to the following coordinate point because a time $\varphi_2^{k(-1)}(t_a)$ corresponds to a time $\varphi_2^{k(-1)}(t_a)$ on an interpolated ECG $f^{k,l}(t)$.

[Formula 12]

$$(\varphi_2^{k(-1)}(t_a), f^{k,l}(\varphi_2^{k(-1)}(t_a))), 0 \le k \le 1, 0 \le l \le 1 \quad (6)$$

In this expression (6), $\varphi_2^{k(-1)}$ is an inverse function of $\varphi_2^k$. The value in the longitudinal axis direction is calculated as follows.

[Formula 13]

$$f(\varphi_2^{k(-1)}(t_a)) = lf_1(\varphi_1^k(\varphi_2^{k(-1)}(t_a))) + (1-l)f_2(\varphi_2^k(\varphi_2^{k(-1)}(t_a))) \quad (7)$$

$$= l(f_1 \circ \varphi_1^k \circ \varphi_2^{k(-1)})(t_a) + (1-l)f_2(t_a)$$

Each annotation to be applied by a person may preferably include at least time information, and thus, it is possible to calculate the point at which the annotation to be applied on an ECG as desired.

<Annotation Prediction Method>

By using the annotation method described above, which is performed on an ECG, it is also possible to predict a position to be annotated. An example will be described with reference to FIG. 7. Suppose that there is a point $A(t_a, f_2(t_a))$ where an annotation is applied on the ECG $f_2(t)$. If $f_2(t)$ is transformed to $f_2'(t)$ (corresponding to $f_2'$ ($\gamma^*(t)$) in FIG. 7) by the alignment process based on $f_1(t)$, the point A is projected to a point A' ($t_a'$, $f_2'$ ($t_a'$)). As described above, $t_a'$ is calculated by the following expression:

[Formula 14]

$$t_a' = \varphi_1^{k(-1)}(t_a) \quad (8)$$

Figure 11:
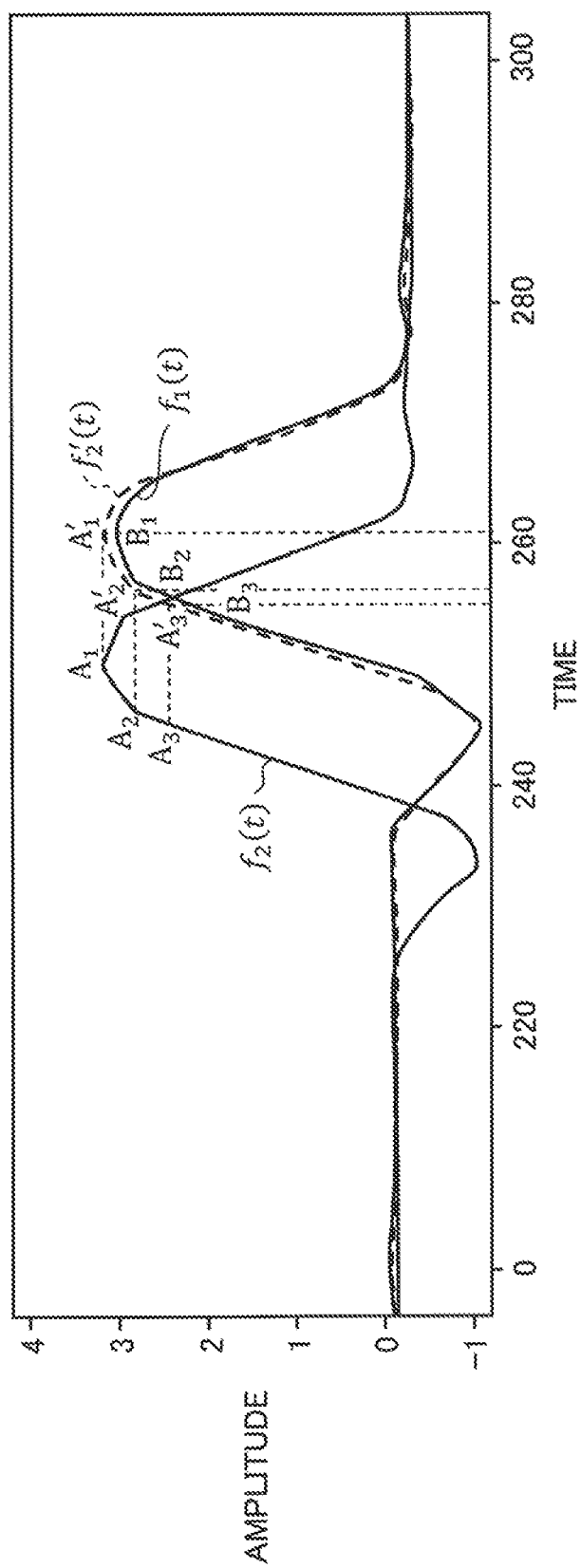
FIG. 11 is a diagram illustrating a result example of an annotation predicting process.

Since $f_1(t)$ and $f_2'(t)$ have already been aligned, a point on $f_1(t)$ corresponding to the point A on $f_2(t)$ is regarded as a point B ($\varphi_2^{1.0(-1)}(t_a)$, $f_1(\varphi_2^{1.0(-1)}(t_a))$) on $f_1(t)$ at the same time $t_a'$ the point A' is located. The alignment process of the ESA is a process for estimating a corresponding point from a viewpoint of shapes of curves. Hence, the point B is regarded as an annotation position estimated with respect to $f_1(t)$. FIG. 11 illustrates an example of an annotation prediction by using this technique.

FIG. 11 is a diagram illustrating a result example of the annotation predicting process. In FIG. 11, an enlarged region including a QRS complex is illustrated.

A function $f_2'$ (t) is obtained by aligning $f_2(t)$ based on $f_1(t)$ as a reference, and hence, the obtained $f_2'(t)$ is aligned with $f_1(t)$. Annotation positions $A_1$, $A_2$, and $A_3$ applied on $f_2(t)$ are projected to annotation positions $A_1'$, $A_2'$, and $A_3'$ on $f_2'$ (t), respectively, with the same amplitude value. Then, annotation positions $B_1$, $B_2$, and $B_3$ are determined on $f_1(t)$ by matching times of the annotation positions $A_1'$, $A_2'$, and $A_3'$ applied on $f_2'$ (t). Among positions $B_1$, $B_2$, and $B_3$ on $f_1(t)$, with respect to an already existing annotation, the applying of an annotation may be omitted.

Figure 12:
FIG. 12 is a diagram illustrating an example of ECG data, to which annotations have been applied.
Figure 12:

FIG. 12 is a diagram illustrating an example of ECG data, to which annotations have been applied. In FIG. 12, an ECG $f_1(t)$ and an ECG $f_2(t)$ correspond to two pieces of data selected from the electro-cardiogram data 51, and an ECG $f_2(t)'$ corresponds to one piece of data in the interpolation data 52, and in particular, corresponds to data, in which the ECG $f_2(t)$ is aligned to the ECG $f_1(t)$.

In the ECTG $f_2(t)$, the annotation A3 is applied to the waveform at time $t_a$, the annotation A2 to the waveform at time $t_b$, and the annotation A1 to the waveform at time $t_e$. These annotations A1 to A3 are applied to the ECG $f_1(t)$.

The ECG $f_2(t)'$ is obtained by transforming the ECG $f_2(t)$ with parameter k=1, in which a phase of the ECG $f_2(t)'$ matches a phase of the ECG $f_1(t)$. Respective positions of the annotations A1 to A3 on the ECG $f_2(t)$ also move along a phase movement. Specifically, the time $t_a$, $t_b$, and $t_c$ of the annotations A1, A2, and A3 on the ECG $f_2(t)$ are projected to times $t_d$, $t_e$, and $t_f$ on the ECG $f_2(t)'$, respectively, and applied annotations are denoted by A1', A2', and A3', respectively.

For the ECG $f_1(t)$, annotations are applied at the same times $t_d$, $t_e$, and $t_f$ as the annotations A1', A2', and A3' applied on the ECGT $f_2(t)'$, and are denoted respectively by B1, B2, and B3. The annotation may be applied at a time other than one at which the annotation already exists on the ECG $f_1(t)$.

The above described procedure for applying the annotation is merely an example. For instance, a missing annotation on each of the ECG $f_1(t)$ and the ECG $f_2(t)$ may be compensated through the interpolated ECG $f_2(t)'$.

Figure 13:
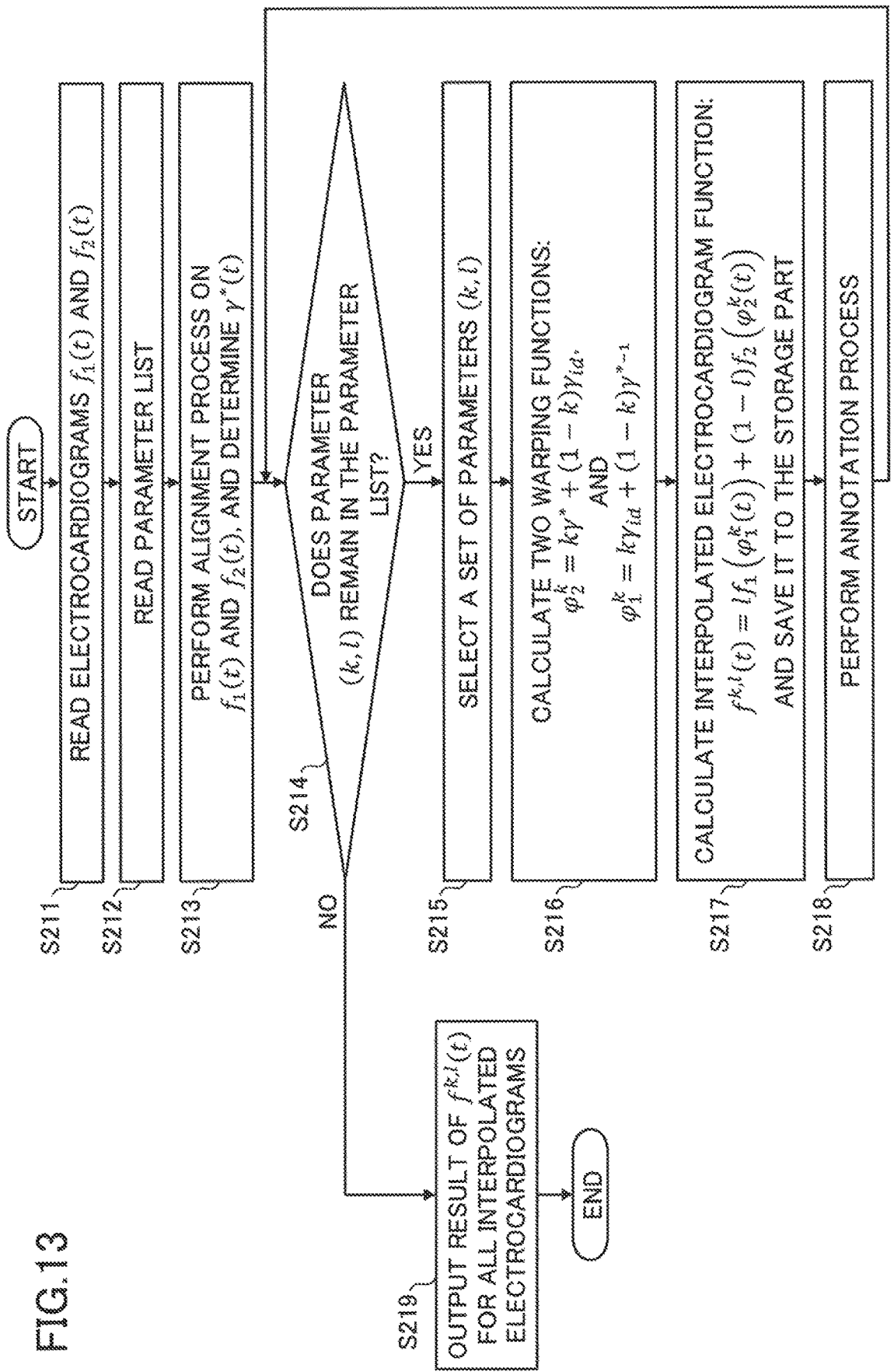
FIG. 13 is a flowchart illustrating a waveform interpolation process.

FIG. 13 is a flowchart illustrating a waveform interpolation process. In FIG. 13, the waveform interpolation part 42 reads the ECG $f_1(t)$ and $f_2(t)$ in response to a notification from the selection part 41 (step S211) and reads the parameter list 53 (step S212).

The parameter list 53 lists all combinations of the parameters "k" and "l", where the parameter "k" indicates a proportional distribution magnitude in the phase direction and the parameter "l" indicates a proportional distribution magnitude in the amplitude direction. The parameters "k" and "l" are values greater than or equal to 0 and less than or equal to 1, and multiple different values are set for each of the parameters "k" and "l". Alternatively, an increment amount or the like in an iterative process may be provided by the user for each of the parameters "k" and "l". Hereinafter, a combination of the parameters "k" and "l" is referred to as parameters (k, l).

The waveform interpolation part 42 performs the alignment process to the ECG $f_1(t)$ and the ECG $f_2(t)$ to determine a warping function $\gamma^*(t)$ for optimizing an alignment (step S213). That is, the optimization problem described above (expression (1.1)) is solved.

The waveform interpolation part 42 determines whether unprocessed parameters (k, l) remain in the parameter list 53 (step S214). When the unprocessed parameters (k, l) remain (YES in step S214), the waveform interpolation part 42 selects one set of parameters (k, l) from the parameter list 53 (step S215), and calculates two warping functions $\varphi_2^k$ and $\varphi_1^k$ (step S216).

That is, among the described expressions (3) and the expressions (4), the following expressions are calculated:

[Formula 15]

$$\varphi_2^k = k\gamma^* + (1-k)\gamma_{id}$$

$$\varphi_1^k = k\gamma_{id} + (1-k)\gamma^{*-1}$$

Next, the waveform interpolation part 42 calculates a function $f^{k,l}(t)$ of the aforementioned interpolated expression (5) using the obtained two warping functions $\varphi_2^k$ and $\varphi_1^k$:

[Formula 16]

$$f_{k,l}(t) = lf_1(\varphi_1^k(t)) + (1-l)f_2(\varphi_2^k(t)).$$

The waveform interpolation part 42 stores obtained values in the storage part 130 (step S217). The waveform interpolation part 42 requests the annotation addition part 43 to apply the annotation, and thus, the annotation addition process is performed (step S218). Next, the waveform interpolation part 42 goes back to step S214, and repeats the above-described process.

When there are no unprocessed parameters (k, l) (NO in step S214), that is, when all combinations are processed, the waveform interpolation part 42 outputs the calculated result of the function $f^{k,l}(t)$ of all interpolated ECGs (step S219). The calculated result for each function $f^{k,l}(t)$ is added as the interpolation data 52 to the training data 57.

In the above-described flowchart, a function calculation is described. In the data generating apparatus 100, with respect to a discrete function value sequence, a spline interpolation or the like is sequentially performed. Also, a result may be discretized as appropriate.

Figure 14:
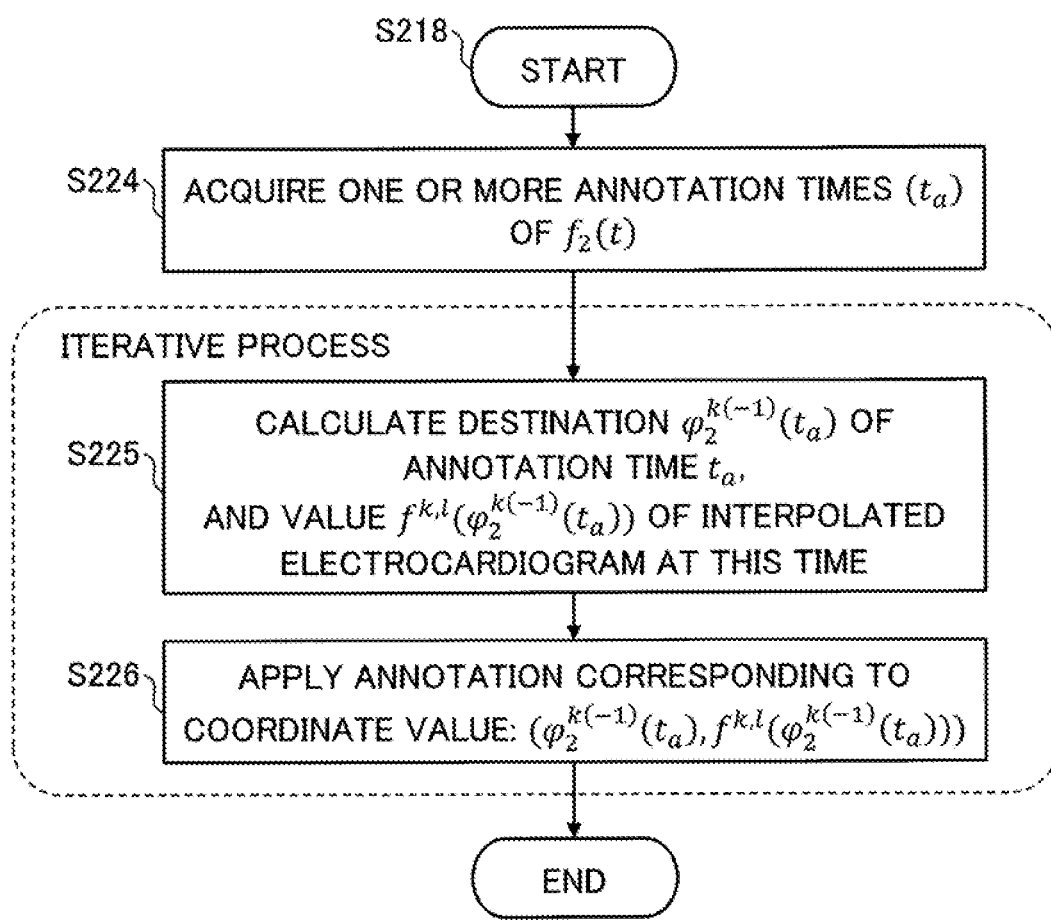
FIG. 14 is a flowchart illustrating a process of adding annotations in step S218 of FIG. 13.

FIG. 14 a flowchart illustrating a process of adding annotations in step S218 of FIG. 13. In FIG. 14, the annotation addition part 43 acquires the annotation time $(t_a)$ of $f_2(t)$ (step S224). The annotation time indicates the time at which the annotation is applied on $f_2(t)$, and multiple annotation times may exist. In a case of multiple annotation times, step S225 and step S226 are repeated for each annotation.

The annotation addition part 43 calculates a destination for projecting the annotation time $t_a$ and a value on an interpolated ECG at a time corresponding to the annotation time $t_a$ (step S225). The destination is determined by $\varphi_2^{k(-1)}(t_a)$ in the above expression (3). The value on the interpolated ECG is obtained by $f^{k,l}(\varphi_2^{k(-1)}(t_a))$ in the above expression (7).

The annotation addition part 43 applies an annotation by corresponding to a coordinate value (step S226). The coordinate value is specified by $(\varphi_2^{k(-1)}(t_a), f^{k,l}(\varphi_2^{k(-1)}(ta)))$. The annotation addition part 43 terminates the annotation addition process when the annotation addition process is conducted for all annotation times.

Not necessarily all interpolation data 52 need to be annotated. In this case, step S218 in FIG. 13 may be omitted, and one or more annotations may be applied to data selected from pieces of the interpolation data 52 after the waveform interpolation is completed.

Figure 15:
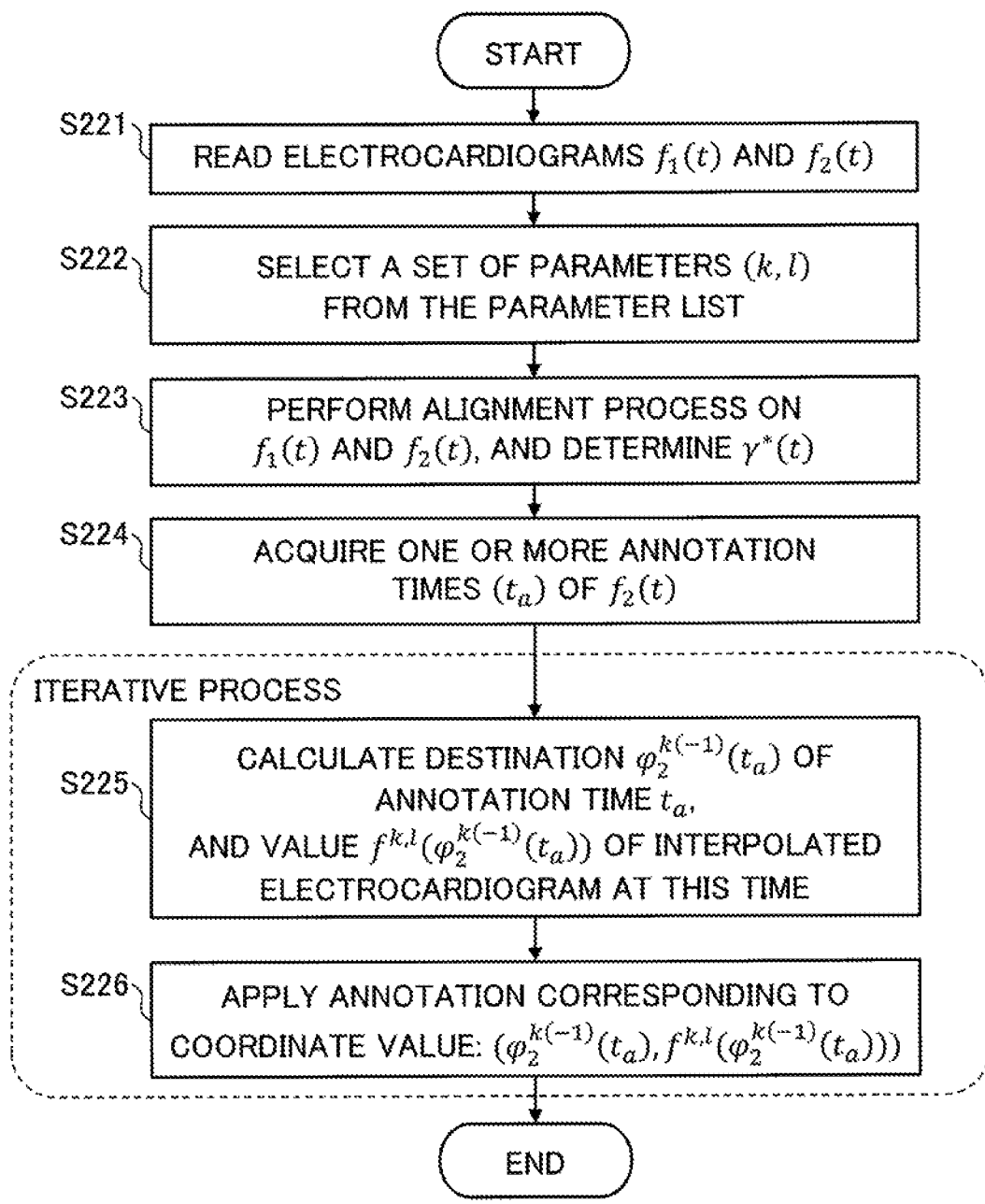
FIG. 15 is a flowchart illustrating another example of the annotation addition process.

FIG. 15 is a flowchart illustrating another example of the annotation addition process. In FIG. 15, the annotation addition part 43 reads the ECG $f_1(t)$ and the ECG $f_2(t)$ upon completing the waveform interpolation process by the waveform interpolation part 42 (step S221), and selects one set of parameters (k, l) from the parameter list 53 (step S222). The selection method may be random or a middle point in the phase direction and a middle point in the amplitude direction are defined beforehand in a predetermined manner.

The annotation addition part 43 performs the alignment process on the ECG $f_1(t)$ and the ECG $f_2(t)$, and determines the warping function $\gamma^*(t)$ for optimizing the alignment (step S223). Steps S224 to S226 are previously described with reference to FIG. 14, and explanations thereof will be omitted here.

Figure 16:
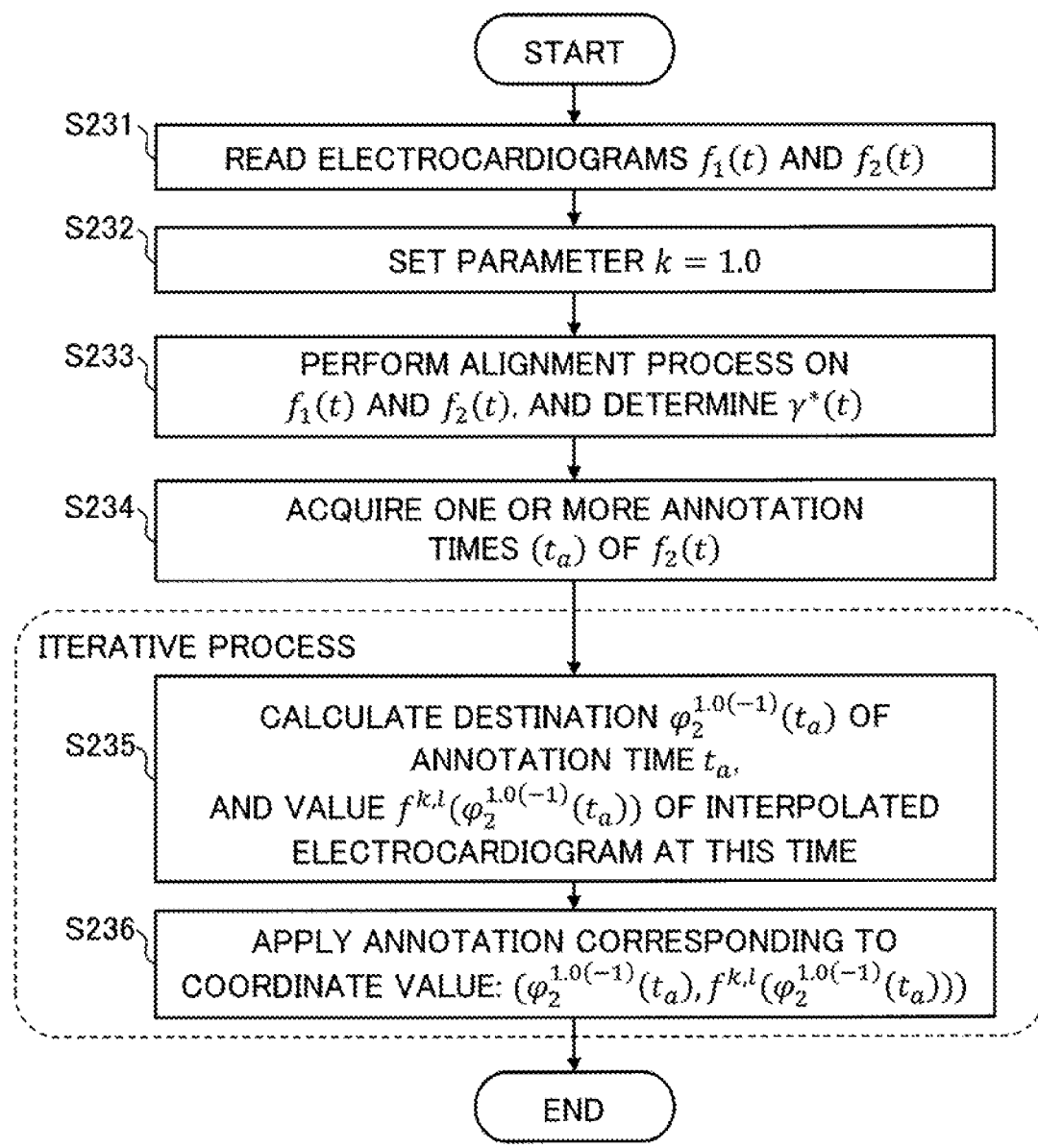
FIG. 16 is a flowchart illustrating the annotation predicting process.

FIG. 16 is a flowchart illustrating the annotation predicting process. In FIG. 16, the annotation prediction part 44 reads the ECG $f_1(t)$ and the ECG $f_2(t)$ as results by causing the selection part 41 to perform the pre-process (a) described above (step S231), and sets the parameter "k" to 1.0 (step S232).

The annotation prediction part 44 performs the alignment process to the ECG $f_1(t)$ and the ECG $f_2(t)$ to determine the appropriate warping function $\gamma^*(t)$ for optimizing the alignment (step S233).

The annotation prediction part 44 acquires the annotation time $(t_a)$ of $f_2(t)$ (step S234). The annotation time indicates the time for $f_2(t)$, at which the annotation is applied, and multiple annotation times may be acquired. In a case of multiple annotation times, step S235 and step S236 are repeated for each acquired annotation time.

The annotation prediction part 44 calculates a destination for projecting the annotation time $t_a$, and calculates a value on the ECG $f_1(t)$ as a prediction subject at the destination where the annotation time is projected (step S235). The destination is determined by $\varphi_2^{k(-1)}(t_a)$ in the above expression (3). The interpolated ECG value is obtained by $f^{k,l}(\varphi_2^{k(-1)}(t_a))$ in the above expression (7).

The annotation prediction part 44 applies an annotation corresponding to a coordinate value (step S236). The coordinate value is specified by $(\varphi_2^{k(-1)}(t_a), f^{k,l}(\varphi_2^{k(-1)}(t_a)))$. The annotation prediction part 44 terminates the annotation predicting process when the annotation predicting process has been completed for all annotation times.

Furthermore, in the annotation process of the embodiment, in a case in which the annotation 3a exists at a part of one piece of the electro-cardiogram data 51, a cut-out region may be one period, and the annotation 3a may be applied at a similar position in each period.

Figure 17A:
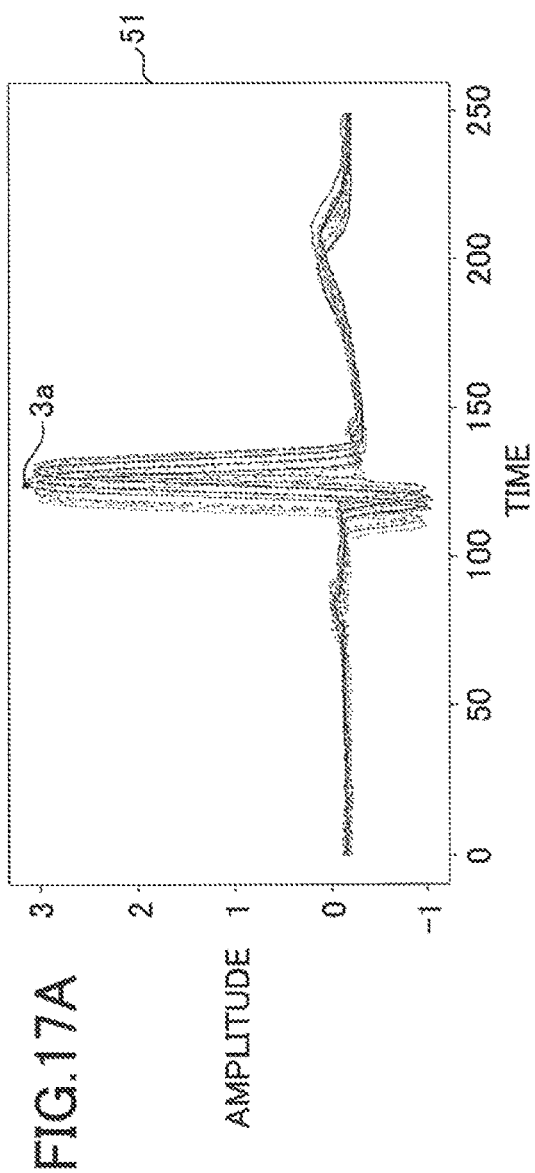
FIG. 17A illustrates a state, in which a plurality of partial waveforms in respective cut-out regions are superimposed with respect to the electro-cardiogram data 51.
Figure 17B:
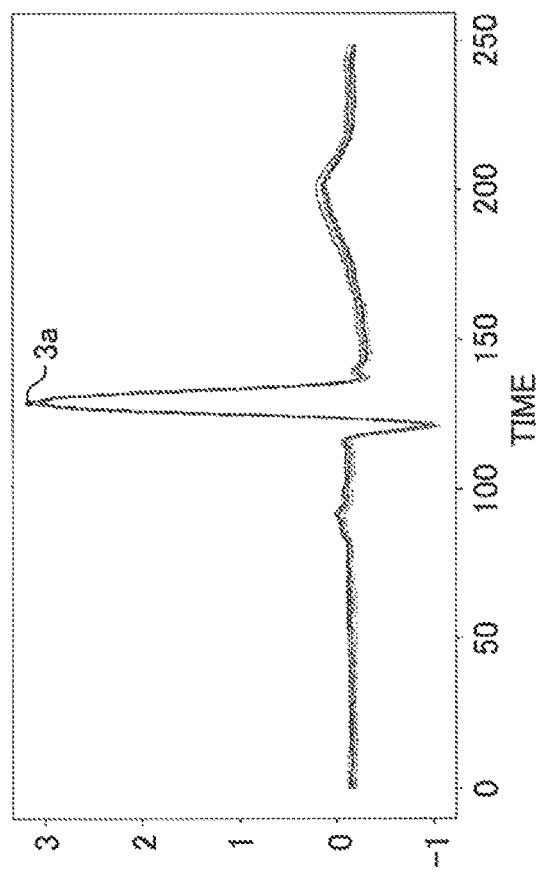
FIG. 17B illustrates the alignment process for the plurality of partial waveforms.

FIG. 17A and FIG. 17B are diagrams illustrating an example of applying an annotation on the ECG data. FIG. 17A illustrates a state, in which a plurality of partial waveforms in respective cut-out regions are superimposed with respect to the electro-cardiogram data 51. FIG. 17B illustrates the alignment process for the plurality of partial waveforms. The time, at which an annotation 3a is applied, may be specified, and the annotation 3a is applied to a position where the time coincides on each of the plurality of partial waveform.

When a partial waveform, to which the annotation 3a has been applied, is denoted by the ECG $f_2(t)$ and each of other partial waveforms is denoted by the ECG $f_1(t)$ for the annotation predicting process described in FIG. 16, it is possible to realize an applying of the annotation 3a to the other partial waveforms in a similar manner. In this case, it is possible to reduce the workload of a person, such as a physician, having specialized knowledge.

As described above, according to the embodiment, the data generating apparatus 100 does not merely generate natural waveform data as human ECGs and expand an amount of the training data, but also applies markings provided by a person having specialized knowledge are applied to the generated waveform data. Therefore, it is possible to improve a learning efficiency.

It is possible to optimize waveform data, to which marking information is applied.

In the embodiment, the annotation 3a is an example of marking information, and a peak or a valley of the element waveform of the ECG is an example of a characteristic point of the waveform data. A set of step S231 and the selection part 41 corresponds to an example of an acquisition part. Step S233 performed by the annotation prediction part 44 corresponds to a portion of a specifying part. A set of steps S234 to S236 performed by the annotation prediction part 44 corresponds to a portion of the generation part.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present invention have been described in detail, it should be understood that the various changes, substitutions, and alterations could be made hereto without departing from the spirit and scope of the invention.

What is claimed is:

1. A data generation method executed by a computer, the data generation method comprising:
   acquiring first waveform data and second waveform data, each of the first waveform data and the second waveform data including marking information at a first position on a waveform;
   specifying a transformation function that transforms the first waveform data to reduce a difference between a first value of a time axis for a first characteristic point in the first waveform data and a second value of the time axis for a second characteristic point, in the second waveform data, corresponding to the first characteristic point; and
   generating third waveform data, in which the marking information is applied at a second position corresponding to the first position in the first waveform data, the second position being determined by using the transformation function.

2. The data generation method as claimed in claim 1, further comprising:
   generating fourth waveform data between the first waveform data and the second waveform data, by at least one of shifting a waveform in a phase direction and of changing a value in an amplitude direction by the transformation function, in order for the first waveform data to be closer to the second waveform data.

3. The data generation method as claimed in claim 2, further comprising:
   applying the marking information at a third position in generated fourth waveform data, the third position corresponding to the first position.

4. The data generation method as claimed in claim 2, further comprising:
   applying the marking information at a third position corresponding to the first position, with respect to a piece of waveform data selected from the generated fourth waveform data.

5. The data generation method as claimed in claim 1, further comprising:
   acquiring the first waveform data and the second waveform data by cutting out different portions from waveform data, in which an appearance pattern of one or more characteristic points is repeated.

6. The data generation method as claimed in claim 1, wherein the first waveform data and the second waveform data correspond to data representing a state of a living body, and
   among the first waveform data and the second waveform data, one piece of data corresponds to data representing a normal state of the living body, and another piece of data corresponds to data representing an abnormal state of the living body.

7. A non-transitory computer-readable recording medium that stores a data generation program that causes a computer to execute a process comprising:
   acquiring first waveform data and second waveform data, each of the first waveform data and the second waveform data including marking information at a first position on a waveform;
   specifying a transformation function that transforms the first waveform data to reduce a difference between a first value of a time axis for a first characteristic point in the first waveform data and a second value of the time axis for a second characteristic point, in the second waveform data, corresponding to the first characteristic point; and generating third waveform data, in which the marking information is applied at a second position corresponding to the first position in the first waveform data, the second position being determined by using the transformation function.

8. An information processing apparatus, comprising:

a memory; and a processor coupled to the memory and the processor configured to acquire first waveform data and second waveform data, each of the first waveform data and the second waveform data including marking information at a first position on a waveform;

specify a transformation function that transforms the first waveform data to reduce a difference between a first value of a time axis for a first characteristic point in the first waveform data and a second value of the time axis for a second characteristic point, in the second waveform data, corresponding to the first characteristic point; and generate third waveform data, in which the marking information is applied at a second position corresponding to the first position in the first waveform data, the second position being determined by using the transformation function.

* * * * *